(12) United States Patent
Currie et al.

(10) Patent No.: US 7,468,362 B2
(45) Date of Patent: *Dec. 23, 2008

(54) CARBONATE AND CARBAMATE MODIFIED FORMS OF GLUCOCORTICOIDS IN COMBINATION WITH $\beta_2$ ADRENERGIC AGONISTS

(75) Inventors: Mark G. Currie, Sterling, MA (US); Steve Jones, Milford, MA (US); Paul Grover, Plainville, MA (US); Chris H. Senanayake, Brookfield, CT (US); Q. Kevin Fang, Wellesley, MA (US)

(73) Assignee: Sepracor Inc., Marlborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/777,830

(22) Filed: Jul. 13, 2007

(65) Prior Publication Data

US 2008/0103119 A1 May 1, 2008

Related U.S. Application Data

(63) Continuation of application No. 11/364,659, filed on Feb. 28, 2006, now Pat. No. 7,253,156, which is a continuation of application No. 10/633,086, filed on Aug. 1, 2003, now abandoned, which is a continuation-in-part of application No. 10/369,828, filed on Feb. 20, 2003, now Pat. No. 7,018,995.

(60) Provisional application No. 60/358,246, filed on Feb. 20, 2002, provisional application No. 60/428,180, filed on Nov. 21, 2002.

(51) Int. Cl.
   A61K 31/58 (2006.01)
   A61K 31/573 (2006.01)
   A61K 31/56 (2006.01)

(52) U.S. Cl. .................. 514/174; 514/179; 514/180; 514/870

(58) Field of Classification Search ............... 514/174, 514/179, 180
   See application file for complete search history.

(56) References Cited

U.S. PATENT DOCUMENTS

| | | | | |
|---|---|---|---|---|
| 3,056,727 | A | 10/1962 | Allais et al. | 167/74 |
| 3,329,570 | A * | 7/1967 | Allais et al. | 514/179 |
| 4,235,887 | A | 11/1980 | Voorhees et al. | 424/180 |
| 5,681,964 | A | 10/1997 | Ashton et al. | 548/491 |

FOREIGN PATENT DOCUMENTS

| | | |
|---|---|---|
| DE | 19541689 | 5/1996 |
| GB | 126929 | 4/1972 |
| GB | 1269291 | 4/1972 |
| WO | WO92/13873 | 8/1992 |
| WO | WO93/11773 | 6/1993 |
| WO | WO95/20567 | 8/1995 |
| WO | WO01/78742 | 10/2001 |
| WO | WO03/070745 | 8/2003 |

OTHER PUBLICATIONS

Charpiot et al. "Disease activated Drugs: A New Concept. for the Treatment of Asthma" *Biorg. Med. Chem.9*, 1793-1805 (2001).
El Masry et al. "Snythesis and Biological Action of Two Glucocorticoid Alkylating Agents" *J. Med. Chem.* 20, 1134-1139 (1977).
Lange et al. "Soluble Steroids I Sugar Derivatives" *J. Pharm. Sci. 51*, 1102-1106 (1962).
Brown et al. "Some 21-Carbamates of Hydrocortisone and Related Compounds" *J. Org. Chem.* 27, 961-963 (1962).
XP008009269; Creticos et al., "Comparison of Triamcinolone Acetonide (TAA), Salmeterol Xinofate (SMT), TAA+SMT, and Placebo (PL) in Mild-Moderate Asthmatics," *European Respiratory Journal*,12 (28), 1565 (1998).
XP001013661; McGavin et al., "Inhaled Budesonide/Formoterol Combination," *Drugs* 61, 71-78 (2001).

* cited by examiner

*Primary Examiner*—Barbara P Badio
(74) *Attorney, Agent, or Firm*—Heslin Rothenberg Farley & Metsisti P.C.

(57) ABSTRACT

Compositions containing $\beta_2$ adrenergic agonists in combination with carbonates and carbonates of the formula

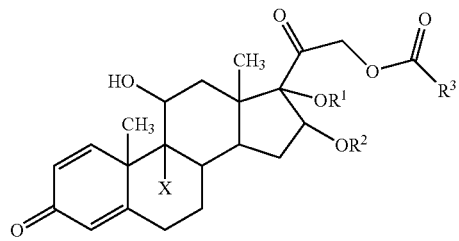

and in combination with related steroid carbonates and carbonates are disclosed. The compositions are useful for treating bronchospasm, for inducing bronchodilator and for treating rhinitis, asthma, and chronic obstructive pulmonary disease (COPD) and inflammatory diseases, particularly by inhalation.

13 Claims, 3 Drawing Sheets

CARBONATE AND CARBAMATE MODIFIED FORMS OF GLUCOCORTICOIDS IN COMBINATION WITH β₂ ADRENERGIC AGONISTS

CROSS REFERENCE TO RELATED APPLICATIONS

This application is a continuation of U.S. patent application Ser. No. 11/364,659 filed Feb. 28, 2006, now U.S. Pat. No. 7,253,156 which is a continuation of U.S. patent application Ser. No. 10/633,086 filed Aug. 1, 2003, now abandoned, which is a continuation in part of U.S. patent application Ser. No. 10/369,828 filed Feb. 20, 2003, now U.S. Pat. No. 7,018,995, which claims the priorities of US provisional applications 60/358,246, filed Feb. 20, 2002, and 60/428,180, filed Nov. 21, 2002. The entire disclosures of all of the prior applications and patents are incorporated herein by reference.

FIELD OF THE INVENTION

The invention relates to methods of treating rhinitis, asthma, and inflammation using carbonate and carbamate derivatives of glucocorticoids in combination with $\beta_2$ adrenergic agonists.

BACKGROUND OF THE INVENTION

Glucocorticoids, in topical, oral and inhaled formulations, are useful for their anti-inflammatory and immunosuppressive activities. Notwithstanding the sophistication of many formulations, many glucocorticoids exhibit significant side-effects that prevent realization of their maximum pharmacologic value. These side-effects stem, in part, from the difficulty of effectively delivering the glucocorticoid drug to a target tissue without increasing systemic concentrations of the drug.

Inhaled glucocorticoids are an effective therapy for the control of asthma, and improvement with steroids is one of the hallmarks of asthma [Barnes, P J (1998) in *Asthma: Basic Mechanisms and Clinical Management* (3rd ed)]. The inhaled glucocorticoids work to reduce the inflammation in either lungs, e.g. for asthma, or nose, e.g. for nasal allergies. Inhaled glucocorticoids are most often administered using a metered dose inhaler (MDI). In the best of circumstances, in controlled clinical settings, only around 30% of the administered dose gets into the lungs. In the general patient population probably only 10% or so of the dose gets into the lungs due to improper use of the inhaler. The rest of the administered drug is deposited in the throat and upper airways, or is swallowed. The drug that is deposited in the throat is responsible for some side effects seen with inhaled glucocorticoids (cough, oropharyngeal candidiasis and dysphonia). For early generation inhaled glucocorticoids, the swallowed drug leads to the same side effects seen with oral glucocorticoids. In light of the tremendous efficacy of inhaled glucocorticoids in asthma, much effort has gone into reducing the side effects from their use. Although newer glucocorticoids (e.g. budesonide, ciclesonide, triamcinolone and fluticasone) exhibit reduced systemic side effects from the swallowed drug—being either poorly absorbed in the gut or subject to extensive inactivation in the liver—they nonetheless display systemic side effects as a result of absorption from the lung into the systemic circulation. The side effects include decreased bone density (Israel, E et al., (2001), *New England Journal of Medicine* 345:941-947 and Wong, C A et al., (2000) *Lancet* 355:1399-1403), which has been correlated with increased risk of fracture. Thus the need still exists for inhaled glucocorticoids with reduced systemic effects.

Several approaches have been suggested to reduce systemic effects. One such approach takes advantage of inactive prodrugs that are activated in the lung tissues. For example, Dietzel et al. [*Prog. Respir. Res.* 31, 91-93 (2001)] have described an isopropyl group esterified at the 21 position of the glucocorticoid core structure. Another approach that has been suggested is the formulation of a glucocorticoid as a liposome. Axelsson et al. in a series of U.S. Pat. Nos. 4,693,999; 5,614,514 and 5,888,995 describe selected glucocorticoids modified for formulation into liposomes by esterification at the 21 position with saturated and mono-unsaturated fatty acids with chain lengths up to 20 carbons.

SUMMARY OF THE INVENTION

It has now been found that by combining the following carbonate and carbamate compounds of Formula I:

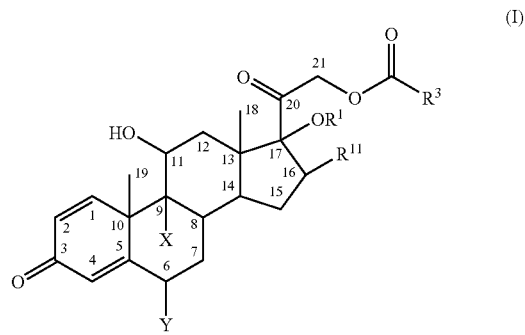

with $\beta_2$ adrenergic agonists, novel drug formulations effective in treating asthma and rhinitis, as well as other respiratory and inflammatory conditions are provided. Furthermore, the new drug compositions provide unexpectedly greater potency for an extended period of time relative to known glucocorticoid alcohols or shorter chain carbonates and carbamates.

In the compounds of Formula I according to the invention:

$R^1$ and $R^2$, independently for each occurrence, represent a hydrogen, lower alkyl or lower acyl, or taken together $R^1$ and $R^2$ form a substituted or unsubstituted ketal;

$R^3$ is —$OR^4$ or —$NR^5R^6$;

$R^4$ is chosen from $C_7$ to $C_{24}$ hydrocarbon, —($C_7$ to $C_{24}$ hydrocarbon)—COOH and —($C_7$ to $C_{24}$ hydrocarbon)—$NR^9R^{10}$;

$R^5$ is hydrogen or $C_7$ to $C_{24}$ hydrocarbon;

$R^6$ is chosen from $C_7$ to $C_{24}$ hydrocarbon and —($C_7$ to $C_{24}$ hydrocarbon)—COOH;

$R^9$ is hydrogen or $C_1$ to $C_{17}$ hydrocarbon;

$R^{10}$ is hydrogen or $C_1$ to $C_{17}$ hydrocarbon;

$R^{11}$ is methyl or —$OR^2$; and

X and Y are independently hydrogen or halogen.

Therefore, in one aspect, the invention relates to pharmaceutical compositions comprising the compounds of Formula I in combination with $\beta_2$ adrenergic agonists.

In another aspect the invention relates to methods for treating bronchospasm, for inducing bronchodilation and for treating rhinitis, asthma, and chronic obstructive pulmonary disease (COPD) and inflammatory diseases and conditions, which comprise administering the compositions containing a compound of Formula I in combination with a $\beta_2$ adrenergic agonist.

In another aspect, the invention relates to pharmaceutical formulations for inhalation comprising the compositions containing a compound of Formula I in combination with a $\beta_2$ adrenergic agonist, a pharmaceutically acceptable fluid for suspension or solution, and, for metered dose inhalers, additionally comprising a propellant.

DETAILED DESCRIPTION OF THE INVENTION

Figure 1:
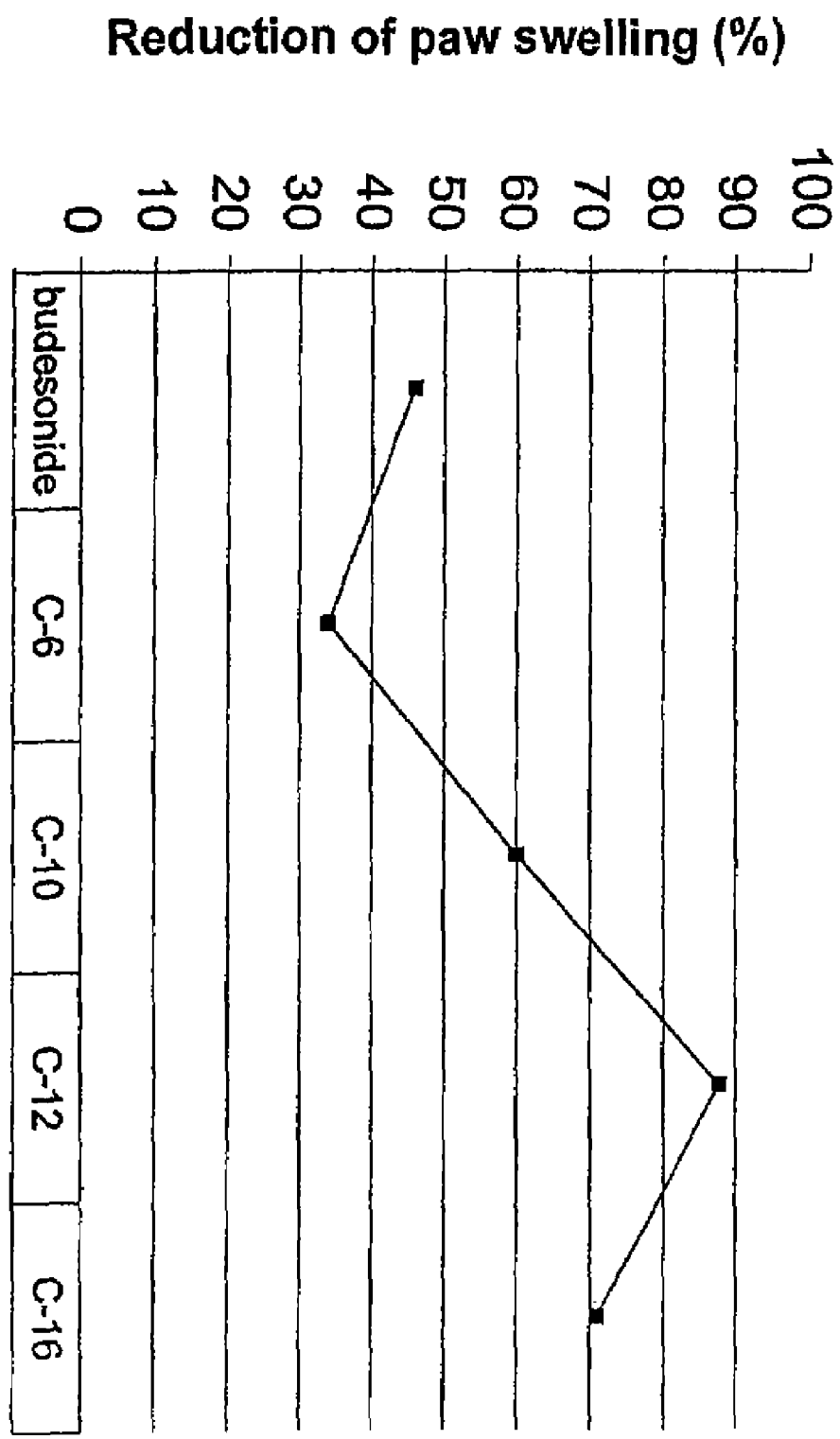
FIG. 1 is a graph of the percent reduction in rat paw edema as a function of the number of carbons in a series of carbamate esters of budesonide.

The invention relates to compositions obtained by combining $\beta_2$ adrenergic agonists with compounds of Formula I:

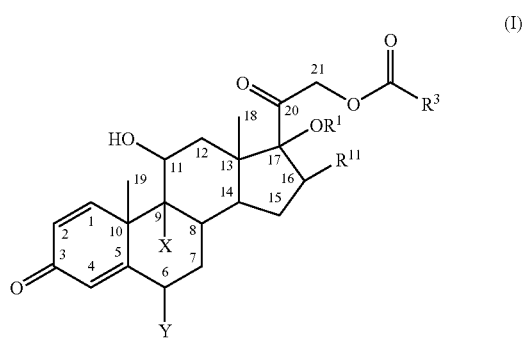

in which the substituents are as defined above. In preferred embodiments the steroid of Formula I has the absolute stereochemistry shown:

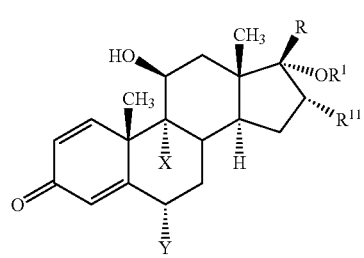

Examples of steroids having the foregoing structure include budesonide, ciclesonide and triamcinolone. The most preferred embodiment of Formula I compounds have structure:

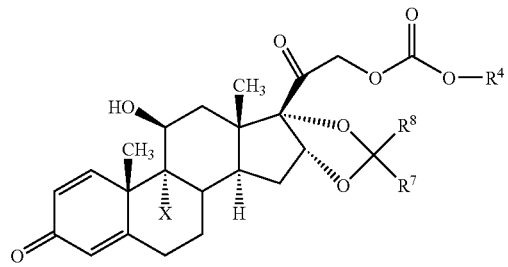

wherein $R^7$ is hydrogen or lower alkyl; and $R^8$ is lower alkyl. In particularly preferred embodiments, $R^4$ is $C_{11}$ to $C_{14}$ alkyl, $C_{12}$ to $C_{24}$ alkyl, $C_{12}$ to $C_{20}$ alkyl, $C_7$ to $C_{24}$ alkyl, $C_8$ to $C_{24}$ alkyl, $C_9$ to $C_{24}$ alkyl, $C_{10}$ to $C_{24}$ alkyl, $C_{11}$ to $C_{24}$ alkyl, $C_8$ to $C_{18}$ alkyl, $C_{10}$ to $C_{16}$ alkyl or $C_8$ to $C_{20}$ alkyl. In preferred embodiments the steroid is budesonide, ciclesonide or triamcinolone. Budesonide dodecyl carbonate is most preferred.

In embodiments of Formula I in which $R^3$ is —$OR^4$ and $R^4$ is —($C_7$ to $C_{24}$ hydrocarbon)—$NR^9R^{10}$, it is preferred that the total number of carbons in $R^3$ be eight to twenty-four. Similarly, in embodiments in which $R^3$ is —$NR^5R^6$, it is preferred that the sum of the number of carbons in $R^5$ plus the number of carbons in $R^6$ be seven to twenty-four. The underlying guideline is that the total number of carbons in the residue $R^3$ is optimally seven to twenty-four, but an amino function could be interposed at any point that results in an $R^3$ residue that is chemically stable in combination with the adjacent $O(C=O)$ residue.

In another particularly preferred embodiment of Formula I, $R^3$ is

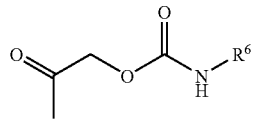

and $R^6$ is $C_{11}$ to $C_{14}$ alkyl, $C_{12}$ to $C_{24}$ alkyl, $C_{12}$ to $C_{20}$ alkyl, $C_7$ to $C_{24}$ alkyl, $C_8$ to $C_{24}$ alkyl, $C_9$ to $C_{24}$ alkyl, $C_{10}$ to $C_{24}$ alkyl, $C_{11}$ to $C_{24}$ alkyl, $C_8$ to $C_{18}$ alkyl, $C_{10}$ to $C_{16}$ alkyl or $C_8$ to $C_{20}$ alkyl.

As used herein, alkyl is intended to include linear, branched, or cyclic hydrocarbon structures and combinations thereof. Preferred alkyl groups are those of $C_7$ to $C_{24}$. Cycloalkyl is a subset of alkyl and includes cyclic hydrocarbon groups, in this case preferably from 6 to 8 carbon atoms. Lower acyl is acyl of one to six carbons, e.g. acetyl, propionyl, isopropanoyl, butanoyl, sec-butanoyl, valeroyl, and hexanoyl.

$C_7$ to $C_{24}$ Hydrocarbon includes alkyl, cycloalkyl, alkenyl, alkynyl, aryl and combinations thereof. Examples include phenethyl, cyclohexylmethyl, camphoryl and naphthylethyl.

The $\beta_2$ adrenergic agonists included in the present compositions as active ingredients with Formula I compounds are non-steroidal bronchodilators or inhibitors of bronchospasm that act selectively on the $\beta_2$ adrenergic receptors. Exemplary useful $\beta_2$ adrenergic agonists include, but are not limited to, the following drug substances: terbutaline, albuterol (also known as salbutamol), fenoterol, hexoprenaline, rimiterol, isoetharine, orciprenaline, metaproterenol, reproterol, clenbuterol, procaterol, carbuterol, tulobuterol, pirbuterol, and bitolterol. Also included are the long acting selective $\beta_2$ adrenergic agonists, such as, formoterol, bambuterol, salmeterol, [(R,S)-1-(4-hydroxy-3-hydroxymethylphenyl)-2-[6-(4-phenylbutoxy)hexylamino]ethanol]. In addition, the acid salts of the aforementioned $\beta_2$ agonists are included, as well as the analogs and mixtures thereof. All of the above listed $\beta_2$ adrenergic agonists are commercially available.

The compounds of Formula I described herein, as well as the $\beta_2$ adrenergic agonists, contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as, their racemic and optically pure forms. Optically active isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included. The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

The abbreviations Me, Et, Ph, Tf, Ts and Ms represent methyl, ethyl, phenyl, trifluoromethanesulfonyl, toluensulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

The term "methods of treating" when used in connection with the present invention means amelioration, prevention or relief from the symptoms and/or effects associated with asthma and rhinitis. The person of ordinary skill in the medical art recognizes that "prevention" of the symptoms and/or effects associated with asthma and rhinitis is not an absolute term. In the medical art it is understood to refer to the prophylactic administration of a drug to substantially diminish the likelihood or seriousness of the condition.

The compositions of the present invention, which include Formula I compounds in combination with $\beta_2$ adrenergic agonists, are useful for treating COPD, asthma, and rhinitis, as well as for treating inflammatory and other respiratory conditions. For administration, a dose providing a weight ratio of Formula I compound to $\beta_2$ adrenergic agonist ranging from 1:6 to 6:1, but more typically 1:1, is generally therapeutically effective.

In general, the compounds having Formula I may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Exemplary syntheses of a budesonide carbonate and a carbamate are shown in Schemes 1 and 2. One skilled in the art will recognize that the syntheses can be adapted to prepare a variety of carbonate or carbamate modified budesonide, ciclesonide, fluticasone or triamcinolone analogs.

Scheme 1.

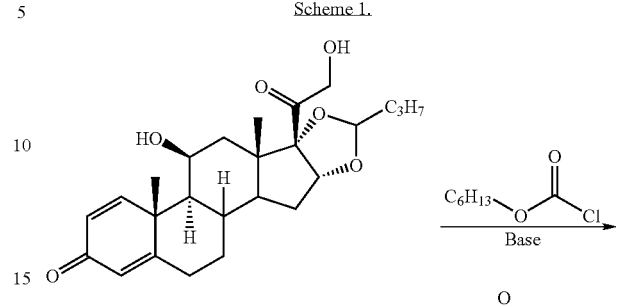

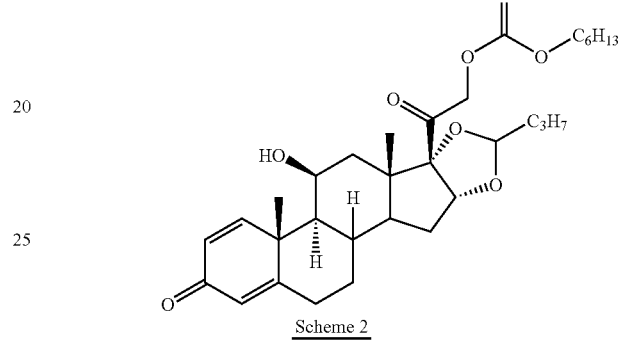

Scheme 2

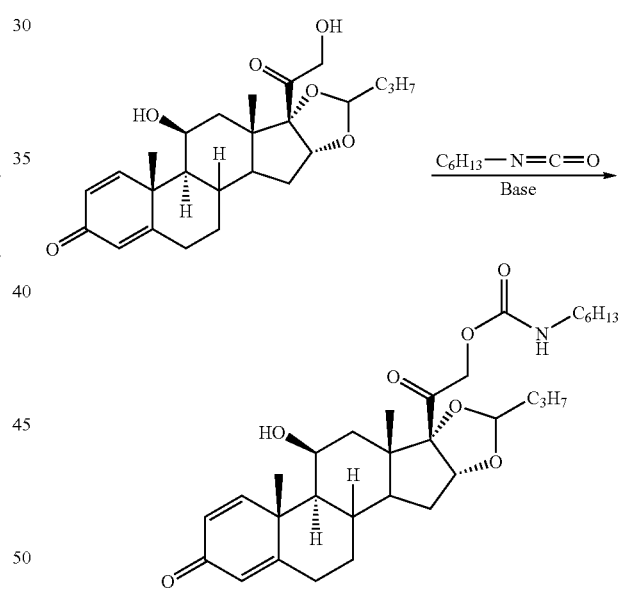

Synthesis of Budesonide Dodecylcarbonate. (Example 2)

To the solution of budesonide (750 mg, 1.74 mmol) in DCM (7.5 mL) was added dodecyl chloroformate (513 mL, 1.617 mmol) and Et$_3$N (533 µL, 3.825 mmol) at room temperature. The reaction mixture was stirred at room temperature for 7 hours. During this 7 hours more dodecyl chloroformate (510 µL, 1.616 mmol) and Et$_3$N (440 µL, 3.18 mmol) were added. The reaction was followed by HPLC. The reaction mixture was poured into water (20 mL) and DCM (10 mL); the aqueous phase was extracted with DCM (10 mL). The combined organic phases were washed with water (10 mL) and brine (10 mL), dried over Na$_2$SO$_4$, filtered, and concentrated in vacuo to provide crude budesonide dodecylcarbonate. The product was purified by chromatography, eluted with Hexane: AcOEt=9:1 to 3:1 to provide 983 mg of 1:1 mixture of epimers (originated from budesonide) (96.78 area % purity on HPLC). $^1$H NMR (CDCl$_3$) δ 0.80-2.25 (m, 45H), 2.36 (d, 1H, 13.4 Hz), 2.58 (t, 1H, 13.2 Hz), 4.19 (t, 2H, 6.7 Hz), 4.52 (bs, 1H), 4.6-5.2 (m, 5H), 6.03 (s, 1H), 6.30 (d, 1H, 10.1 Hz), 7.29 (d, 1H, 10.1 Hz). $^{13}$C NMR (CDCl$_3$) δ 14.21, 14.38, 17.22, 17.35, 17.50, 17.78, 21.35, 22.94, 25.86, 28.83, 29.45, 29.60, 29.74, 29.80, 29.88, 30.57, 31.24, 32.16, 33.18, 33.68, 34.26, 35.26, 37.36, 41.17, 41.41, 44.24, 46.18, 47.61, 50.01, 53.14, 55.41, 55.52, 69.12, 69.18, 70.11, 70.22, 82.32, 83.57, 97.76, 98.62, 104.88, 108.63, 122.83, 128.24, 156.14, 169.81, 169.92, 186.74, 202.16 and 203.46. Mass spectrum (m/e) 643 (M$^+$).

Synthesis of Budesonide Hexadecylcarbonate. (Example 7)

To the solution of budesonide (431 mg, 1.0 mmol) in DCM (4.5 mL) was added heaxdecyl chloroformate (655 μL, 2.0 mmol) and Et$_3$N (512 μL, 3.7 mmol) at room temperature. After reaction mixture was stirred at room temperature over night, it was poured into water (20 mL) and DCM (10 mL); the aqueous phase was extracted with DCM (10 mL). The combined organic phases were washed with water (10 mL) and brine (10 mL), dried over Na$_2$SO$_4$, filtered, and concentrated in vacuo to provide crude budesonide hexadecylcarbonate. The product was purified by chromatography, eluted with Hexane: AcOEt=9:1 to 3:1 to provide 432 mg of 1:1 mixture of epimers (originated from budesonide) (99.38 area % purity on HPLC). $^1$H NMR (CDCl$_3$) δ 0.80-2.40 (m, 53H), 2.56 (dt, 1H, 13.1 and 4.6 Hz), 4.30 (t, 2H, 6.7 Hz), 4.5-5.2 (m, 7H), 6.00 (s, 1H), 6.26 (d, 1H, 10.1 Hz), 7.3 (d, 1H, 10.1 Hz). $^3$C NMR (CDCl$_3$) δ 14.16, 14.18, 14.34, 17.10, 17.27, 17.39, 17.71, 21.21, 22.88, 25.81, 28.79, 29.41, 29.56, 29.70, 29.76, 29.87, 30.54, 31.19, 32.11, 33.08, 33.59, 34.23, 35.19, 37.28, 40.68, 40.98, 44.37, 46.08, 47.52, 50.00, 53.07, 55.39, 55.49, 68.98, 69.73, 69.83, 69.95, 70.04, 82.10, 83.38, 97.71, 98.58, 104.70, 108.51, 122.57, 127.91, 155.08, 156.85, 170.48, 170.59, 186.84, 186.88, 202.10 and 203.38. Mass spectrum (m/e) 699 (M$^+$).

Synthesis of Budesonide Decylcarbonate. (Example 8)

To the solution of budesonide (431 mg, 1.0 mmol) in DCM (4.5 mL) was added decyl chloroformate (460 μL, 2.0 mmol) and Et$_3$N (512 μL, 3.7 mmol) at room temperature. After the reaction mixture was stirred at room temperature over night, it was poured into water (20 mL) and DCM (10 mL); the aqueous phase was extracted with DCM (10 mL). The combined organic phases were washed with water (10 mL) and brine (10 mL), dried over Na$_2$SO$_4$, filtered, and concentrated in vacuo to provide crude budesonide decylcarbonate. The product was purified by chromatography, eluted with Hexane: AcOEt=9:1 to 3:1 to provide 348 mg of 1:1 mixture of epimers (originated from budesonide) (99.22 area % purity on HPLC). $^1$H NMR (CDCl$_3$) δ 0.85-2.24 (m, 42H), 2.36 (dd, 1H, 13.4 and 2.9 Hz), 2.59 (dt, 1H, 13.5 and 4.5 Hz), 4.18 (t, 1H, 6.7 Hz), 4.51 (s, 1H), 4.6-5.2 (m, 5H), 6.03 (s, 1H), 6.30 (d, 1H, 10.1 Hz), 7.49 (d, 1H, 10.1 Hz). $^{13}$C NMR (CDCl$_3$) δ 14.14, 14.17, 14.31, 17.06, 17.24, 17.36, 17.68, 21.19, 22.83, 25.78, 28.76, 29.37, 29.40, 29.66, 30.52, 31.16, 32.04, 33.05, 33.56, 34.22, 35.16, 37.25, 40.58, 40.89, 44.38, 46.06, 47.49, 49.98, 53.05, 55.38, 55.48, 68.90, 68.94, 69.65, 69.75, 69.92, 70.01, 82.05, 83.34, 97.69, 98.56, 104.65, 108.47, 122.51, 127.84, 155.04, 156.96, 170.61, 170.71, 186.84, 186.89, 202.08 and 203.37. Mass spectrum (m/e) 615 (M$^+$).

Synthesis of Budesonide Butylcarbamate. (Example 6)

To the solution of budesonide (500 mg, 1.16 mmol) in DCM (5.0 mL) was added butyl isocyanate (144 μL, 1.28 mmol) and DMAP (312 mg, 2.55 mmol) at room temperature. The reaction mixture was stirred at room temperature for 24 hours. During this 24 hours more butyl isocyanate (72 μL, 0.64 mmol) and DMAP (156 mg, 1.27 mmol). The reaction was followed by HPLC. The reaction mixture was poured into water (20 mL) and DCM (10 mL); the aqueous phase was extracted with DCM (10 mL). The combined organic phases were washed with water (10 mL) and brine (10 mL), dried over Na$_2$SO$_4$, filtered, and concentrated in vacuo to provide crude budesonide butylcarbamate. The product was purified by chromatography, eluted with Hexane: AcOEt=9:1 to 3:1 to provide 560 mg of 1:1 mixture of epimers (originated from budesonide) (99.22 area % purity on HPLC). $^1$H NMR (CDCl$_3$) δ 0.82-2.7 (m, 30H), 3.06-3.20 (m, 3H), 4.45 (m, 1H), 4.58 (t, 1H, 4.5 Hz), 4.75-5.36 (m, 5H), 5.99 (s, 1H), 6.24 (d, 1H, 10.1 Hz), 7.29 (d, 1H, 10.1 Hz). $^{13}$C NMR (CDCl$_3$) δ 13.98, 14.08, 14.22, 17.09, 17.30, 17.37, 17.73, 20.09, 20.28, 21.26, 30.56, 31.22, 32.11, 32.59, 33.13, 33.65, 34.27, 35.23, 37.34, 40.30, 40.73, 40.99, 41.17, 44.37, 46.09, 47.49, 50.01, 53.15, 55.43, 55.52, 67.82, 69.82, 69.93, 82.11, 83.37, 97.84, 98.75, 104.66, 108.43, 122.61, 127.97, 155.94, 156.03, 156.79, 170.45, 170.56, 186.95, 203.89 and 205.21.

Synthesis of Budesonide 2-Dimethylaminoethyl Carbonate. (Example 20)

To the solution of budesonide (600 mg, 1.394 mmol) in DCM (5.0 mL) was added CDI (249 mg, 1.53 mmol) at RT. After 3 hr stirring, N,N-dimethylethanolamine (308 μL, 3.07 mmol) was added at room temperature. After the reaction mixture was stirred at room temperature for 3.5 hours, it was poured into water (20 mL) and DCM (10 mL); the aqueous phase was extracted with DCM (10 mL). The combined organic phases were washed with water (10 mL) and brine (10 mL), dried over Na$_2$SO$_4$, filtered, and concentrated in vacuo to provide crude budesonide 2-dimethylaminoethyl carbonate. The product was purified by chromatography, eluted with AcOEt, then AcOEt: MeOH=98:2 to 95:5 to provide 307 mg of 1:1 mixture of epimers (originated from budesonide) (98.49 area % purity on HPLC). $^1$H NMR (CDCl$_3$) δ 0.80-2.55 (m, 29H), 3.69 (bs, 1H), 4.17 (t, 2H, 5.8 Hz), 4.42 (bs, 1H), 4.4-4.95 (m, 3H), 5.05 (dd, 1H, 12.5 and 7.2 Hz), 5.92 (s, 1H), 6.28 (d, 1H, 10.1 Hz), 7.29 (d, 1H, 10.1 Hz). $^{13}$C NMR (CDCl$_3$) δ 14.16, 14.21, 17.08, 17.20, 17.37, 17.69, 21.22, 30.52, 31.18, 32.10, 33.06, 33.60, 34.28, 35.16, 37.24, 40.65, 40.94, 44.46, 45.86, 46.23, 47.64, 49.99, 53.11, 55.36, 55.45, 57.56, 66.27, 66.30, 69.34, 69.45, 70.14, 70.18, 82.14, 83.41, 97.76, 98.62, 104.64, 108.42, 122.48, 127.73, 154.92, 157.26, 157.37, 170.75, 170.89, 187.00, 187.08, 201.97 and 203.29.

(5)

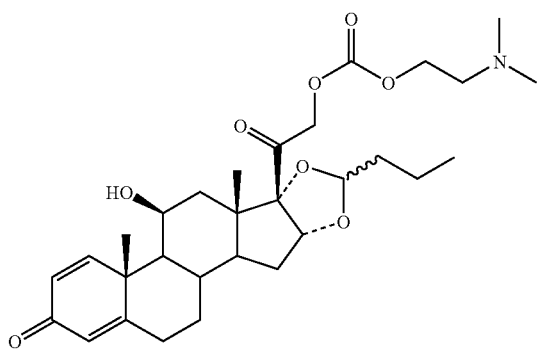

The following compounds were synthesized as described above:

| Example | Name | mol. Wt. |
|---|---|---|
| 1 | Budesonide isobutylcarbonate | 530.65 |
| 2 | Budesonide dodecylcarbonate | 642.87 |
| 3 | Budesonide hexylcarbonate | 558.71 |
| 4 | Budesonide dibutylcarbamate | 585.77 |
| 5 | Dexamethasone dodecylcarbonate | 604.8 |
| 6 | Budesonide butylcarbamate | 529.67 |
| 7 | Budesonide hexadecylcarbonate | 698.98 |
| 8 | Budesonide decylcarbonate | 614.81 |
| 9 | Budesonide hexylcarbonate | 558.71 |
| 10 | Budesonide dodecylcarbonate | 642.86 |
| 11 | Budesonide nonylcarbonate | 600.78 |
| 12 | Budesonide octycarbonate | 586.76 |
| 13 | Budesonide undecylcarbamate | 627.85 |
| 14 | Budesonide heptylcarbonate | 572.73 |
| 15 | Budesonide 11-dimethylaminoundecylcarbonate | 671.9 |
| 16 | Budesonide phytolcarbonate | 753.07 |
| 17 | Budesonide farnesolcarbonate | 678.90 |
| 18 | Budesonide geraniolcarbonate | 610.78 |
| 19 | Budesonide nerolcarbonate | 610.78 |

For administration to treat asthma, rhinitis, COPD and respiratory conditions, the drug of Formula I in combination with one or more $\beta_2$ agonists, is suitably inhaled from a nebulizer, from a pressurized metered dose inhaler or as a dry powder from a dry powder inhaler (e.g. sold as TURBU-HALER®) or from a dry powder inhaler utilizing gelatin, plastic or other capsules, cartridges or blister packs.

A diluent or carrier, generally non-toxic and chemically inert to the medicaments, e.g. lactose, dextran, mannitol or glucose or any additives that will give the medicaments a desired taste, can be added to the powdered medicaments.

For drugs such as $\beta_2$ adrenergic agonists to be absorbed by the alveoli of the lungs, the particle size of the drug is normally reduced to less than about 10 micrometers, preferably between about 0.5 micrometers and about 5 micrometers.

Formulations and devices for nebulizers, metered dose inhalers and dry powder inhalers are well known to those skilled in the art. In formulations where the active ingredients are in a suspension, it is important that the particles be below 20 μm in size and preferably below 5 μm in size. This may be achieved by micronization, crystallization, spray drying or other known techniques.

The solvent or suspension agent utilized for nebulization may be any pharmacologically suitable fluid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both inorganic salts, such as alkali metal or ammonium halogen salts e.g. sodium chloride, potassium chloride or organic salts, such as potassium, sodium and ammonium salts of organic acids, e.g., ascorbic acid, citric acid, acetic acid, tartaric acid, etc. may be used for this purpose.

Other excipients and additives may be added to the formulation. The active ingredients may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid etc.; a complexing agent such as EDTA or citric acid and salts thereof; or an antioxidant such as vitamin E or ascorbic acid. These may be used alone or together to stabilize the active ingredients. Preservatives can also be added such as benzalkonium chloride or benzoic acid and salts thereof. Surfactant may be added particularly to improve the physical stability of suspensions. These include lecithins, disodium dioctylsulphosuccinate, oleic acid and sorbitan esters.

The active ingredients may also be suspended or dissolved in a liquified propellant, sealed in a container with a metering valve and fitted into an actuator. Such metered dose inhalers are well known in the art. The metering valve may meter 10 to 500 μL and preferably 25 to 150 μL.

The propellants used may be halocarbons, hydrocarbons or other liquified gasses. The most frequently used are trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-125), heptafluoropropane (HFA-227ea), perfluoropropane, perfluorobutane, perfluorpentane, butane, isobutane, and pentane. In particular, tetrafluoroethane (HFA-134a) and heptafluoropropane (HFA-227ea) and mixtures thereof are used.

As well as propellant, formulations may contain other excipients. Surfactant may be added particularly to improve the physical stability of suspensions and valve performance. These include lecithins, disodium dioctylsulphosuccinate, oleic acid and sorbitan esters. Cosolvents may also be added to improve solubility of surfactant in propellant or modify the pharmacological performance. These include alcohols and glycols, e.g., ethanol, isopropylalcohol, glycerol, propylene glycol, polyethylene glycol, etc., or mixtures thereof. Further excipients may be added to improve performance or taste, e.g., fatty acids and salts thereof such as magnesium stearate, menthol oil etc.

Dry powder inhalers include devices which meter the drugs from a chamber within the device or those that deliver premetered doses utilizing gelatin, plastic or other capsules, cartridges, or blister packs and/or strips.

Furthermore, the two active ingredients of the present compositions, i.e. compounds of Formula I and $\beta_2$ adrenergic agonists, may be administered simultaneously, in a single dosage form, or-they may be separately, but contemporaneously administered. As used herein, "contemporaneously" means that they are administered such that the peak serum levels of the two medicaments occur within four hours of one another. Usually, the closer to simultaneous peak serum levels, the better.

Compounds of Formula I as described above were tested in the following assay for biological activity. The WI-38 human lung fibroblast line was obtained from the ATCC (catalog number 75-CCL) and maintained in Basal Medium Eagle with Earle's salts (GibcoBRL product number 21010-046) supplemented with 2 mM glutamine and 10% fetal calf serum at 37° C. in a 7% $CO_2$ (balance air), humidified atmosphere. One week before experiments were done, the WI-38 cells were seeded into 48-well tissue culture dishes and maintained in media containing 10% fetal calf serum. The cells were used when confluent. The day before the experiment the cells were fed fresh media containing 10% fetal calf serum (0.25 mL per well). On the day of the experiment the media was removed from the cells and 0.25 mL of media containing 5% fetal calf serum added.

The rat alveolar macrophage cell line RAW 264.7 was obtained from the ATCC (catalog number 71-TIB) and maintained in Dulbecco's Modified Eagle Medium (GibcoBRL product number 11960-044) supplemented with 2 mM glutamine, 1 mM sodium pyruvate and 10% fetal calf serum at 37° C. in a 10% $CO_2$ (balance air), humidified atmosphere. One week before experiments were done, the WI-38 cells were seeded into 48-well tissue culture dishes and maintained in media containing 10% fetal calf serum. The cells were used when confluent. The day before the experiment the cells were fed fresh media containing 10% fetal calf serum (0.25 mL per well). One the day of the experiment the media was removed from the cells and 0.25 mL of media containing 5% fetal calf serum added.

To determine the $IC_{50}$ values for the compounds, 1 to 1000 dilutions were made of the 5 mM stock solutions in DMSO to give 5 uM solutions. These solutions were serially diluted 1:2 in DMSO to give a series of 12 dilutions ranging from 5 uM to 2.4 nM. 0.0025 mL aliquots of the 12 dilutions were added to wells of the WI-38 cells to give final compound concentrations ranging from 50 nM to 0.024 nM. The cells were stimulated by addition of 0.001 mL of 0.025 ug/mL recombinant human Interleukin-1β (IL-1β-Calbiochem catalog number 407615) in 0.1% bovine serum albumin in phosphate buffered saline. The cells were incubated for 24 hours and the supernatants harvested. The level of $PGE_2$ in the supernatants was assayed using a commercial Enzyme Immuno Assay (EIA) kit (Cayman Chemical catalog number 514010) after diluting 1:10 in EIA buffer according to the manufacturer's directions. The data from these experiments was fit to a 4 parameter logistic function using the $IC_{50}$ routine in the Grafit 4 program (Erithecus software). $IC_{50}$ values determined in this manner were: budesonide 0.20 nM; budesonide isobutylcarbonate 0.12 nM; budesonide dodecylcarbonate 0.53 nM; budesonide hexylcarbonate 0.14 nM.

The compounds of Formula I were also tested in vivo in a rat paw edema model [Hirschelmann, R. and Bekemeier, H., *Int J Tissue React* 6, 471-475 (1984)], which persons of skill in the art accept as predictive of efficacy in treating asthma and rhinitis in humans.

Rat Paw Edema Protocol: Male Sprague Dawley rats Rj: SD (IOPS Han) (CEJ, France) weighing between 140 and 160 grams were used in the studies. Animals were housed in a temperature (19.5-24.5° C.), relative humidity (40-70%) and 12-hour light/dark cycle (light 6:00 a.m. to 6:00 p.m.)-controlled room, with ad libitum access to filtered tap-water and standard pelleted laboratory chow (U.A.R., France) throughout the studies. Carrageenan lambda type IV (Sigma, France) was prepared as a 2% (w/v) solution in saline. Compounds to be tested were dissolved in dimethylsulfoxide (DMSO) such that the indicated doses were in a final volume of 0.05 mL. Doses were expressed as mg/paw free active substance. From 17 to 19 hours before the studies the rats were fasted with free access to water. The paw volumes of the left hindpaws of the rats were measured using an electronic plethysmometer type 7140 (Ugo Basile—Italy) at time=0. Paw edema was then induced by injection of 0.05 mL of 2% carrageenan solution into the left hindpaws of the rats. Immediately after injection of the carrageenan, compounds in DMSO or vehicle alone were injected into the same paw in a volume of 0.05 mL in a blind and random fashion.

The paw volumes were measured at 1.5 hours, 3 hours, 4.5 hours and 24 hours after administration of the compounds. The edema volume of each rat at each time point was expressed as the change from the initial paw volume (time=0). A total of 5 rats were used for each compound dose and the average edema volume calculated for each dose. The anti-inflammatory effect in treated groups was expressed as the percent inhibition of edema volume compared to the vehicle-treated group at 1.5 hours, 3 hours, 4.5 hours and 24 hours.

The results are shown in FIG. 1, in which the efficacies of equimolar doses (equivalent to 10 µg per paw of budesonide) are compared at 24 hours. Budesonide itself reduces swelling by 46%. The formation of a carbonate ester at C21 decreases the efficacy of budesonide when the ester is $C_6$ or smaller. Unexpectedly, at $C_6$ the curve reverses, and the efficacy increases. Thus, although one would expect $C_7$ to be less efficacious than $C_6$, in fact it is surprisingly found more efficacious, and the $C_{10}$ carbonate is 30% more efficacious than budesonide itself. The correlation between numbers of carbons in the carbonate ester and efficacy reaches a peak at $C_{12}$ with an 88% reduction of swelling.

Other carbonates showed similar behavior. The phytol (Example 16) and farnesol (Example 17) carbonates exhibited normal onset of action and maximum activity at 24 hours of 69 and 86 percent respectively. The amine-terminal alkylcarbonate, Example 15, exhibited a maximum activity at 24 hours of 73 percent.

Figure 2:
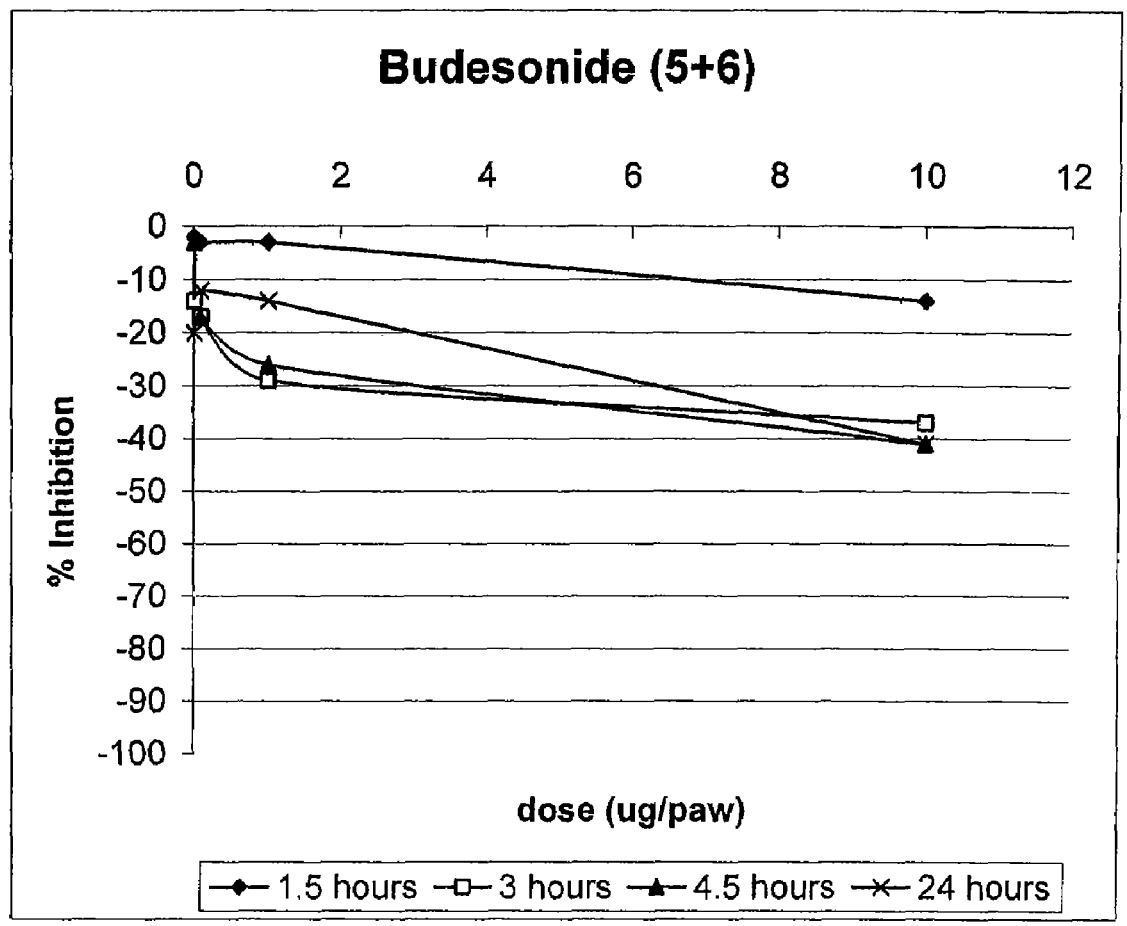
FIG. 2 is a graph of the percent reduction in rat paw edema as a function of the dose of budesonide at four time intervals.
Figure 3:
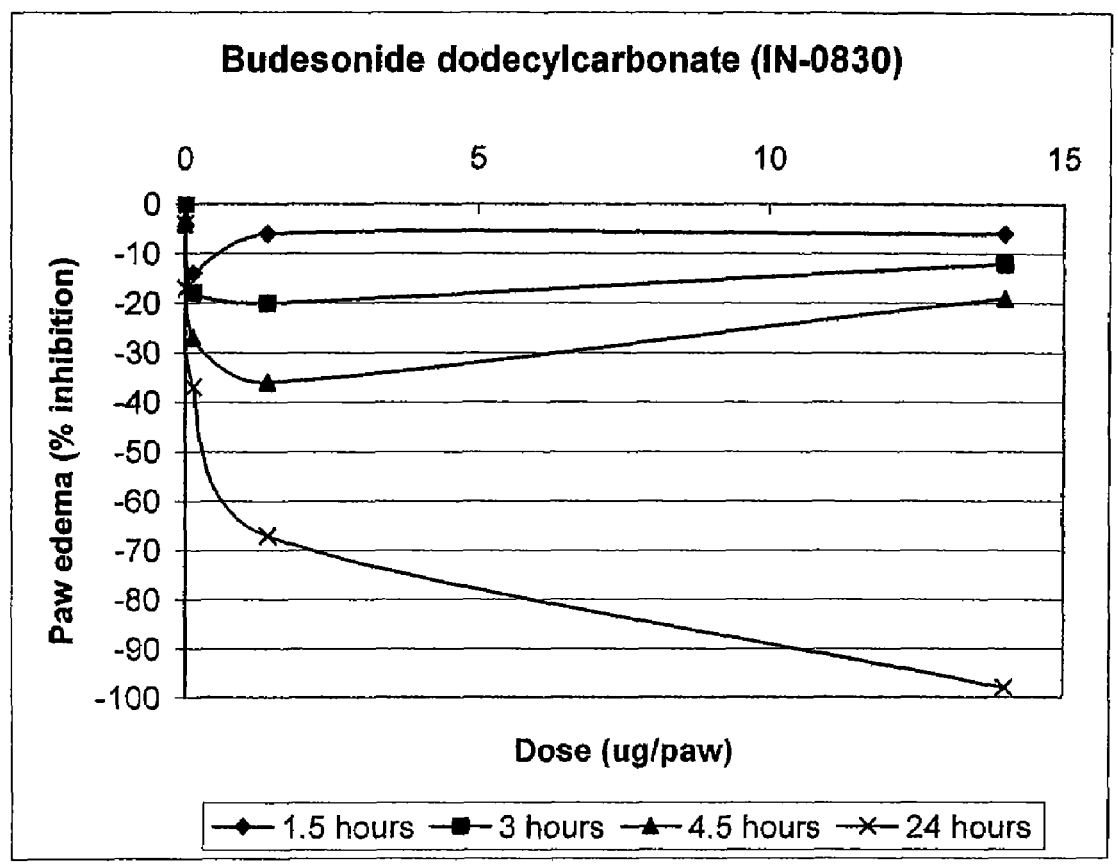
FIG. 3 is a graph of the percent reduction in rat paw edema as a function of the dose of budesonide dodecylcarbonate at four time intervals.

The enhanced effect of the carbonates and carbamates compared to the parent steroid is most dramatic at the 24-hour observation, as can be seen by comparing FIGS. 2 and 3, in which budesonide carbonate is compared to budesonide.

The invention claimed is:

1. A method of reducing edema, comprising: administering to a subject in need an effective amount of a compound of Formula I:

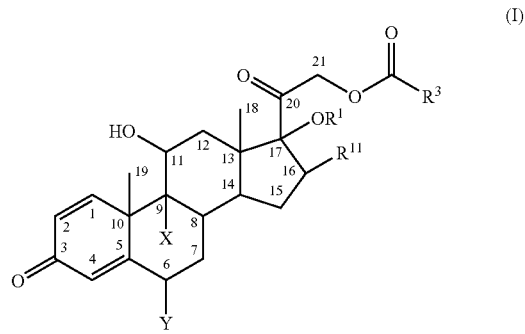

wherein
$R^1$ and $R^2$, independently for each occurrence, represent lower alkyl or lower acyl, or taken together $R^1$ and $R^2$ form a substituted or unsubstantiated ketal;
$R^3$ is —$OR^4$ or —$NR^5R^6$;
$R^4$ is chosen from $C_7$ to $C_{24}$ hydrocarbon, —($C_7$ to $C_{24}$ hydrocarbon)—$NR^9R^{10}$;
$R^5$ is hydrogen or $C_7$ to $C_{24}$ hydrocarbon;
$R^6$ is chosen from $C_7$ to $C_{24}$ hydrocarbon and —($C_7$ to $C_{24}$ hydrocarbon)—COOH;
$R^9$ is hydrogen or $C_1$ to $C_{17}$ hydrocarbon;
$R^{10}$ is hydrogen or $C_1$ to $C_{17}$ hydrocarbon;
$R^{11}$ is methyl or —$OR^2$; and
X and Y are independently hydrogen or halogen.

2. A method according to claim 1, wherein the compound has formula:

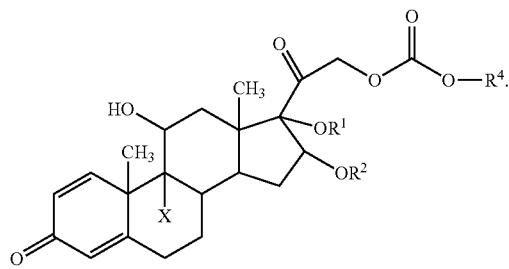

3. A method according to claim 2, wherein the compound has formula:

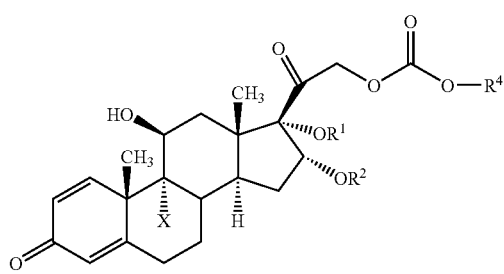

wherein X is hydrogen or fluorine.

4. A method according to claim 3, wherein the compound has formula

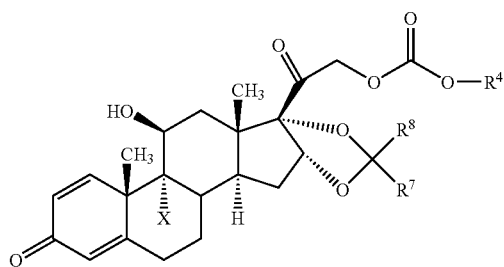

wherein
- $R^7$ is hydrogen or lower alkyl; and
- $R^8$ is lower alkyl.

5. A method according to claim 1, wherein the compound has formula

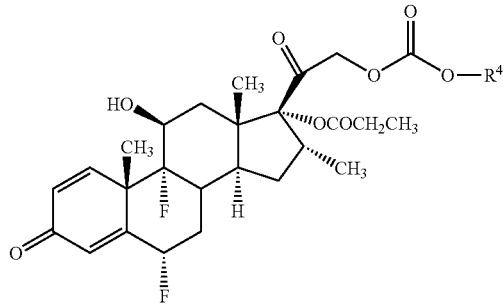

wherein
- $R^4$ is chosen from $C_7$ to $C_{24}$ hydrocarbon, —($C_7$ to $C_{24}$ hydrocarbon)—COOH, and —($C_7$ to $C_{24}$ hydrocarbon)—$NR^9R^{10}$;
- $R^9$ is hydrogen or $C_1$ to $C_{17}$ hydrocarbon; and
- $R^{10}$ is hydrogen or $C_1$ to $C_{17}$ hydrocarbon.

6. A method according to claim 1, wherein in the compound of formula I, $R^4$ is $C_7$ to $C_{24}$ alkyl.

7. A method according to claim 1, wherein the compound has formula:

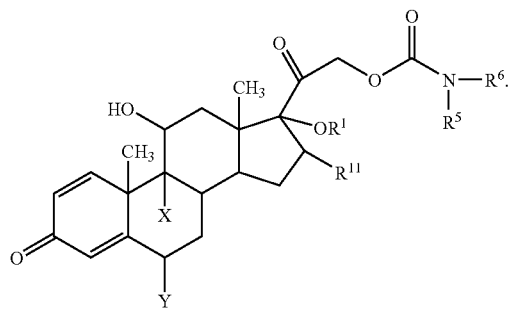

8. A method according to claim 7, wherein the compound has formula:

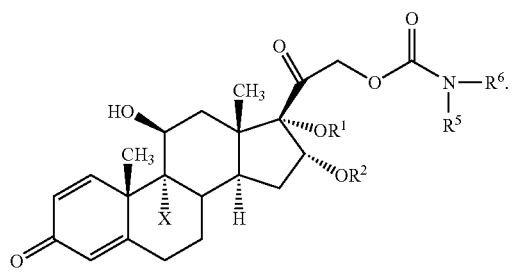

9. A method according to claim 8, wherein the compound has formula

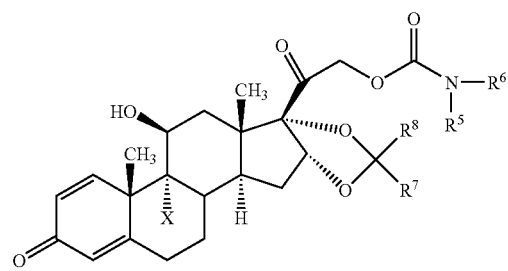

wherein
- $R^7$ is hydrogen or lower alkyl; and
- $R^8$ is lower alkyl.

10. A method according to claim 7, wherein the compound has formula

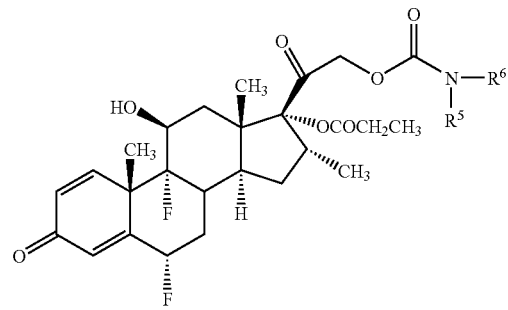

wherein
R⁵ is hydrogen or C₇ to C₂₄ hydrocarbon; and
R⁶ is chosen from C₇ to C₂₄ hydrocarbon and —(C₇ to C₂₄ hydrocarbon)—COOH.
11. A method according to claim 7, wherein in the compound R⁵ is hydrogen or lower alkyl.
12. A method according to claim 7, wherein in the compound R⁶ is C₇ to C₂₄ alkyl.
13. A method according to claim 3, wherein the compound has formula
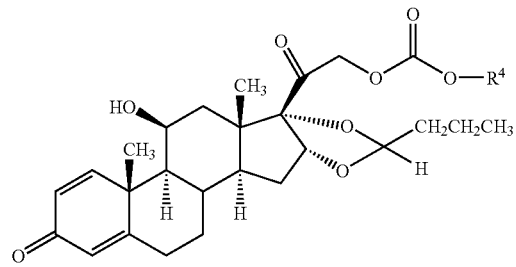
and R⁴ is n-dodecyl.
* * * * *

UNITED STATES PATENT AND TRADEMARK OFFICE
CERTIFICATE OF CORRECTION

PATENT NO. : 7,468,362 B2  
APPLICATION NO. : 11/777830  
DATED : December 23, 2008  
INVENTOR(S) : Currie et al.

Page 1 of 1

It is certified that error appears in the above-identified patent and that said Letters Patent is hereby corrected as shown below:

In the Abstract (57): Delete "for inducing bronchodilator and" and insert -- for inducing bronchodilation and --

In the Claims:

Claim 1, Column 12, Line 43: Delete "$R^4$ is chosen from $C_7$ to $C_{24}$ hydrocarbon,- $C_7$ to $C_{24}$ hydrocarbon)-$NR^9R^{10}$;" and insert -- $R^4$ is chosen from $C_7$ to $C_{24}$ hydrocarbon,- ($C_7$ to $C_{24}$ hydrocarbon)-COOH and ($C_7$ to $C_{24}$ hydrocarbon)-$NR^9R^{10}$ --

Signed and Sealed this

Seventh Day of April, 2009

JOHN DOLL  
*Acting Director of the United States Patent and Trademark Office*